United States Patent [19]

Kozempel et al.

[11] Patent Number: 5,895,814
[45] Date of Patent: Apr. 20, 1999

[54] CONTINUOUS PROCESS FOR THE PRODUCTION OF LACTULOSE FROM LACTOSE USING BORIC ACID AS A COMPLEXSATION AGENT

[75] Inventors: Michael F. Kozempel, Hatfield; Kevin B. Hicks, Malvern, both of Pa.; Michael J. Kurantz, Maple Shade, N.J.; James C. Craig, Maple Glen, Pa.

[73] Assignee: The United States of America, as represented by the Secretary of Agriculture, Washington, D.C.

[21] Appl. No.: 08/510,065

[22] Filed: Aug. 1, 1995

[51] Int. Cl.$^6$ .................................................. C07H 1/00
[52] U.S. Cl. .................................. 536/124; 536/127
[58] Field of Search ........................ 536/18.6, 124, 536/127

[56] References Cited

U.S. PATENT DOCUMENTS 4,273,922  6/1981  Hicks ........................................ 536/125

OTHER PUBLICATIONS

Hicks and Parrish, "A New Method for the Preparation of Lactulose from Lactose", *Carbohydrate Research*, vol. 82, pp. 393–397 (1980).

Kozempel and Kurantz, "The Isomerization Kinetics of Lactose to Lactulose in the Presence of Borate", *J. Chem. Tech. Biotechnol.*, vol. 59, pp. 25–29 (1994).

Hicks et al., "Synthesis and High–Performance Liquid Chromatography of Maltulose and Cellobiulose", *Carbohydrate Research*, vol. 112, pp. 37–50 (1983).

Hicks et al., Removal of Boric Acid and Related Compounds from Solutions of Carbohydrates with Borun–Selective Resin (IRA–743), *Carbohydrate Research*, vol. 147, pp. 39–48 (1986).

Kozempel and Kurantz, "A Continuous Reactor System for Production of Lactulose", *J. Chem. Tech. Biotechnol.*, vol. 59, pp. 265–269 (1994).

*Primary Examiner*—Elli Peselev
*Attorney, Agent, or Firm*—M. Howard Silverstein; John D. Fado; Janelle S. Graeter

[57] ABSTRACT

A method is described for the preparation of lactulose by isomerizing lactose to lactulose, followed by complexing lactulose to boric acid. The isomerization reaction is carried out in alkaline solution, and it is followed by splitting the lactulose-borate complex in acidic solution and separating the two components. Separation is achieved by crystallizing boric acid, filtering the crystals out of the product mixture, evaporating the product mixture to form a concentrate, recirculating the concentrate to the crystallization step where it is mixed with fresh reaction mixture in order to provide volume and nuclei for the crystallization of the boric acid in the reaction mixture, then passing the resulting mixture through another filtration step followed by an additional separation step by column chromatography.

9 Claims, 4 Drawing Sheets

CONTINUOUS PROCESS FOR THE PRODUCTION OF LACTULOSE FROM LACTOSE USING BORIC ACID AS A COMPLEXSATION AGENT

BACKGROUND OF THE INVENTION

1. Field of the Invention

Lactulose, or 4-O-β-D-galactopyranosyl-D-fructose, is a synthetic disaccharide which is synthesized by the isomerization of lactose, or 4-O-β-D-galactopyranosyl-D-glucose, a widely available natural disaccharide. Current processes, however, result in low yields which are difficult and expensive to purify. Thus, the high cost of production and difficulty of preparation have provided an incentive to develop an effective and efficient preparation method. This invention relates to a continuous process for isomerizing lactose to lactulose with boric acid as a complexing agent which provides a high-quality product at a cost substantially lower than that currently available.

2. Description of the Relevant Art

Lactulose was first prepared by a Lobry deBruyn-Alberda van Ekenstein alkaline isomerization of lactose in dilute calcium hydroxide solution (Montgomery and Hudson. 1930. *J. Am. Chem. Soc.* vol. 52, pp. 2102–2106). Other strong alkalis such as sodium hydroxide and potassium hydroxide and strong organic bases have also been utilized in the isomerization reaction. These methods resulted in low yields, however, due to numerous side reactions which lead to the formation of degradation by-products difficult to separate from the reaction mixture. The by-products also imparted a brownish color to the lactulose syrup, and purification steps were necessary not only for their removal but also for that of unreacted starting materials and calcium ions as well.

Subsequent methods for producing lactulose utilized complexing reagents to shift the pseudo-equilibrium established during base-catalyzed isomerization in favor of the ketose and to prevent degradative side reactions. The use of aluminate (U.S. Pat. No. 3,546,206 issued Dec. 8, 1970) and borate ions (Mendicino, J. F. 1960. *J. Am. Chem. Soc.*, vol. 82, pp. 4975–4070; Carubell, R. 1966. *Carbohydr. Res.* vol. 2 pp. 480–485) have been reported for this purpose with varying degrees of effectiveness. The lactulose yield is higher and the product more pure (U.S. Pat. No. 3,546,206, supra; Mendicino, supra), however, both reagents are very difficult to remove from the reaction mixture. In addition a borate:sugar ration of 50:1 (as reported by Mendicino, supra) is required for optimal yield of product, thereby substantially increasing the difficulty of removing borate from the reaction mixture after isomerization is complete.

Base-catalyzed isomerizations have also been carried out utilizing amines as catalysts. Ammonia (Hough et al. 1953. *J. Chem. Soc.* pp. 2005–2009) has been successfully employed for converting lactose to lactulose; however, both primary and secondary amines have resulted in the formation of by-products such as glycosylamines (Ellis and Honeyman. 1955. *Adv. Carbohydr. Chem.* vol. 10, pp. 95–168) and Amadori (Hodge, J. E. 1955. *Adv. Carbohydr. Chem.* vol. 10, pp. 169–205) compounds. The use of the teritary amine triethylamine avoided this problem (U.S. Pat. No. 3,514,327 issued May 26, 1970) since the amine did not form adducts with reducing sugars; however, there was considerable alkaline degradation associated with the process. The combination of the treatment of lactose in the presence of borate (at a molar ratio of 1:1) with tertiary amine (Hicks and Parrish. 1980. *Carbohydr. Res.* vol. 82, pp. 393–397; Hicks, U.S. Pat. No. 4,273,922 issued Jun. 16, 1981) minimized degradative side-reactions and resulted in high yields of lactulose with a minimal use of borate.

Carobbi et al. (U.S. Pat. No. 4,536,221 issued Aug. 20, 1985) disclosed the isomerization of lactose to lactulose in the presence of a basic magnesium salt and sodium hydrosulphite. Extensive purification is required, however, in order to remove unreacted lactose, Mg and Na ions and the related anions. The addition of hydrosulphite results in a reduction in the amount of degradation products in the reaction mixture. Sulphite, bisulphite and phosphite ions are believed to react with these products to form sugar sulphonic acids and sugar phosphonic acids. These compounds pose disposal problems because they are environmentally undesirable however, therefore they must subsequently be removed. Alternatively, de Haar et al. (U.S. Pat. No. 5,026,430 issued Jun. 25, 1991) taught the addition of hydrogen peroxide or sodium chlorite to reaction mixtures containing sulphite, bisulphite or phosphite. Hydrogen peroxide serves to oxidize the degradation products of lactulose to carboxylic acids which can be removed by ion exchangers. Sodium chlorite is also an effective coreagent, however, due to the requirement for sodium hydroxide in the isomerization reaction, corrosive compounds such as chlorine and chlorodioxide are formed.

While the conversion of lactose to lactulose in the presence of borate has proven to be particularly effective, a commercially feasible process has remained elusive due to the difficulty of effectively separating the lactulose product from the reaction mixture.

SUMMARY OF THE INVENTION

We have discovered a novel process which allows for overcoming the above identified problems by operating the reaction and recovery systems continuously, thereby increasing the efficiency of the procedure.

In accordance with this discovery, it is an object of the invention to provide a novel method of producing lactulose which is effectively separated from the boric acid used to complex with and stabilize the product.

DETAILED DESCRIPTION OF THE INVENTION

Figure 1:
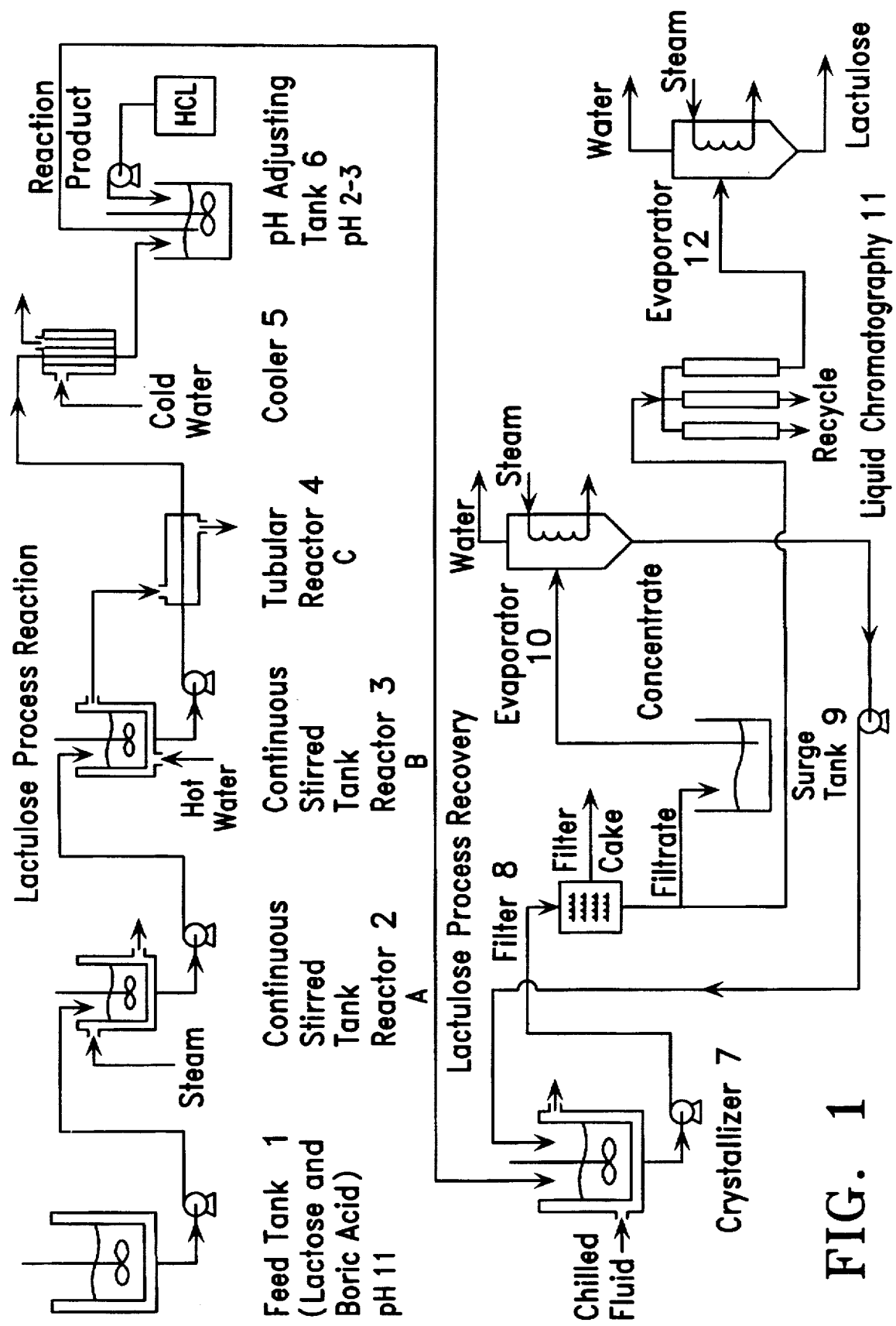
FIG. 1 is a flow diagram of a continuous system for the preparation of lactulose.

The instant invention describes a commercially feasible process to make lactulose based on the boric acid complexation reaction described by Hicks (U.S. Pat. No. 4,273,922, supra, herein incorporated by reference; Hicks et al. *Carbohydr. Res.* 1983. vol. 112, pp. 37–50). The process is carried out in two phases, i.e. a reaction phase for the isomerization of lactose to lactulose and a recovery phase for the removal of boric acid from the product mixture. The development of the process occurred in three parts—a study of the isomerization kinetics of lactose to lactulose in the presence of boric acid, the development of a continuous reactor system for the production of lactulose and the development of a system for purifying the product. FIG. 1 illustrates an effective system which may be utilized for carrying out the entire process comprising a reactor system having several reactors for the preparation of the product and a recovery system for first removing the bulk of the boric acid, then a final separation of the product.

In the presence of base (NaOH) lactose isomerises to lactulose in low yield with multiple side reactions giving numerous by-products; however the addition of boric acid to the reaction results in the formation of a lactulose-borate complex which is stable under basic conditions. Hicks and Parrish, 1980, supra, showed that the combination of lactose and boric acid in a molar ratio of about 1:1 in the presence of tertiary amines produced lactulose in high yields. The complexation of boric acid with lactulose shifted the equilibrium established during isomerization in favor of lactulose and minimized degradative side-reactions. It was also shown that NaOH can be substituted for the tertiary amines (Hicks et al., 1983, supra; Hicks et al. 1984. *J. Agr. & Food Chem.* vol. 32, pp. 288–292).

In the kinetic studies (Kozempel and Kurantz. 1994. *J. Chem. Tech. Biotechnol.* vol. 59, pp. 25–29, herein incorporated by reference) the isomerization of lactose to lactulose was modeled as two consecutive but separate reactions. The first was the equilibrium conversion of lactose to a borate-lactulose complex, plus galactose and other by-products, through competing first order reactions. The second reaction was the disruption of the complex, releasing borate and lactulose from the complex when the mixture was acidified. The rate controlling reaction was determined to be the isomerization of lactose to lactulose in the presence of NaOH and the formation of a boric acid-lactulose complex.

In the reaction, lactose apparently isomerizes initially to lactulose, most of which is instantly complexed by the boric acid. Lactulose breaks down in alkaline solutions into a mixture of galactose and α- and β-isosaccharinic acids, and a small amount of the lactulose goes to these unwanted by-products instead of complexing. When the reaction mixture is acidified, the complex instantly splits, releasing lactulose and boric acid. The complex is extremely stable at high pH; however, the disruption of the complex is very quick at low pH.

Figure 2:
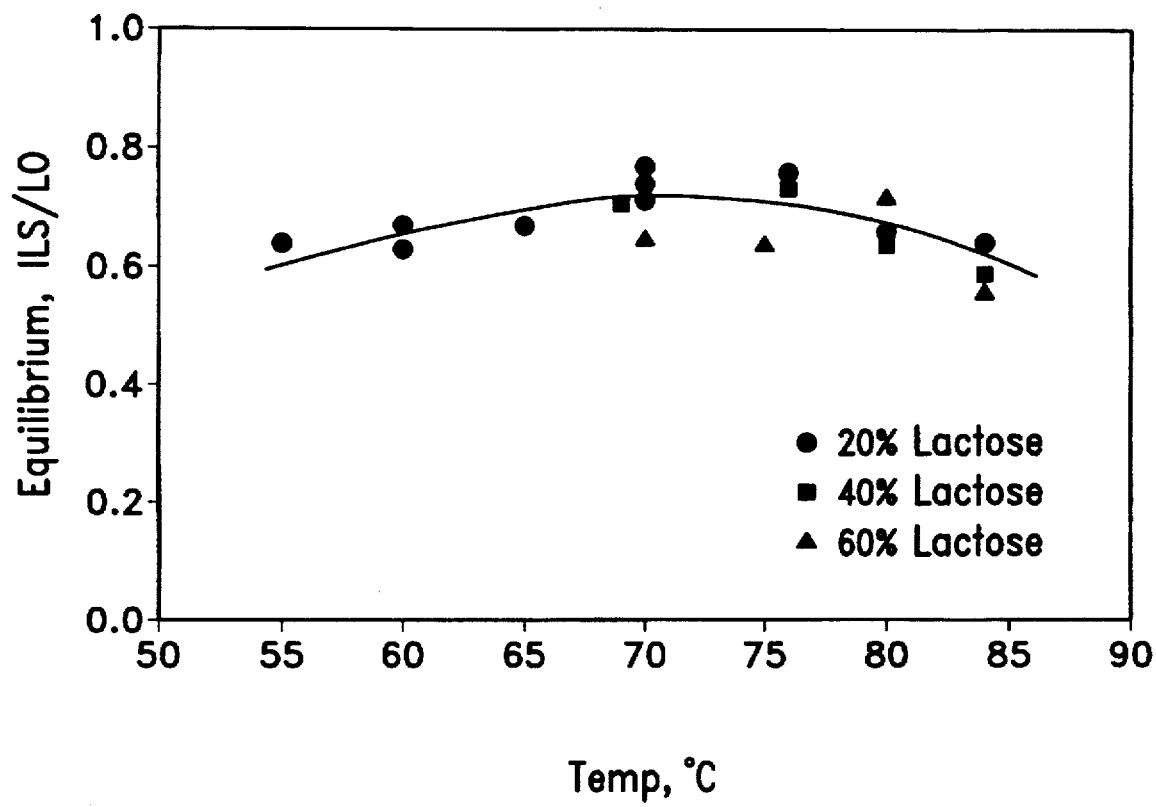
FIG. 2 shows the effect of temperature and lactose concentration on the equilibrium value for lactulose; the molar ratio $H_3BO_3$/lactose=1.0, pH 11.
Figure 3:
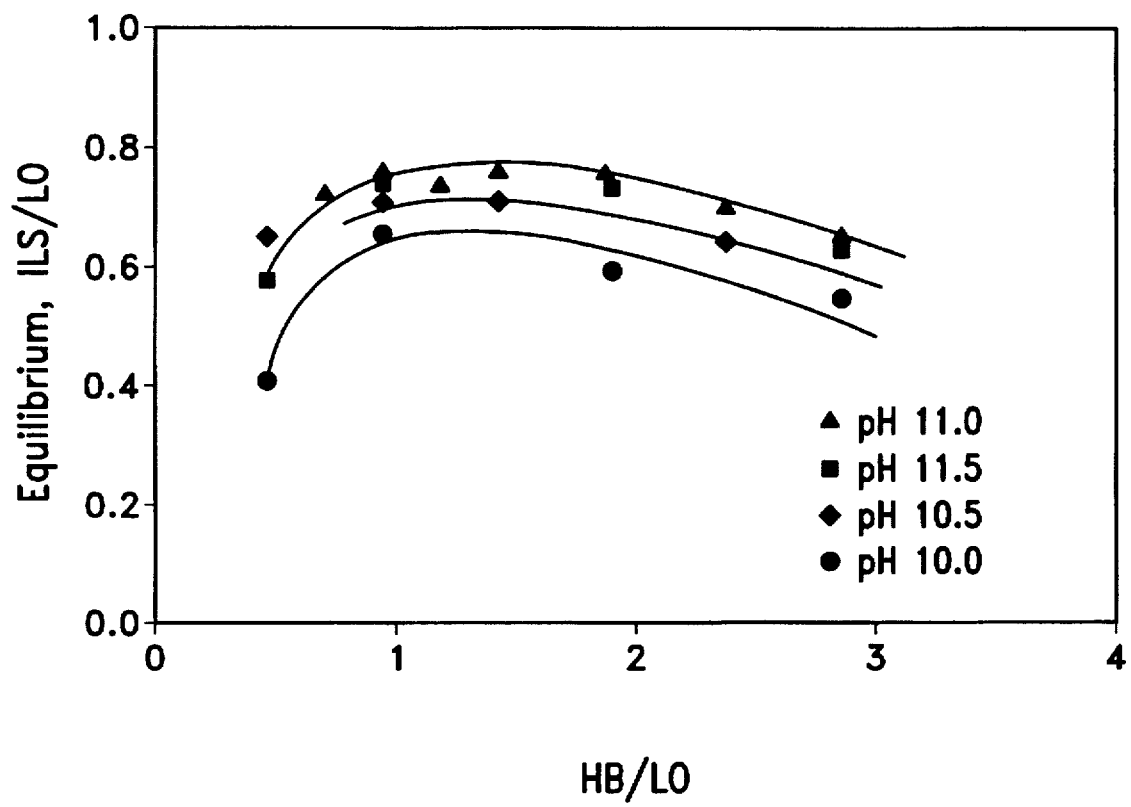
FIG. 3 shows the effect of molar ratio of complexing agent to lactose on equilibrium value for lactulose at 70° C. HB=boric acid concentration, $L_o$=initial lactose concentration; 20 wt %.
Figure 4:
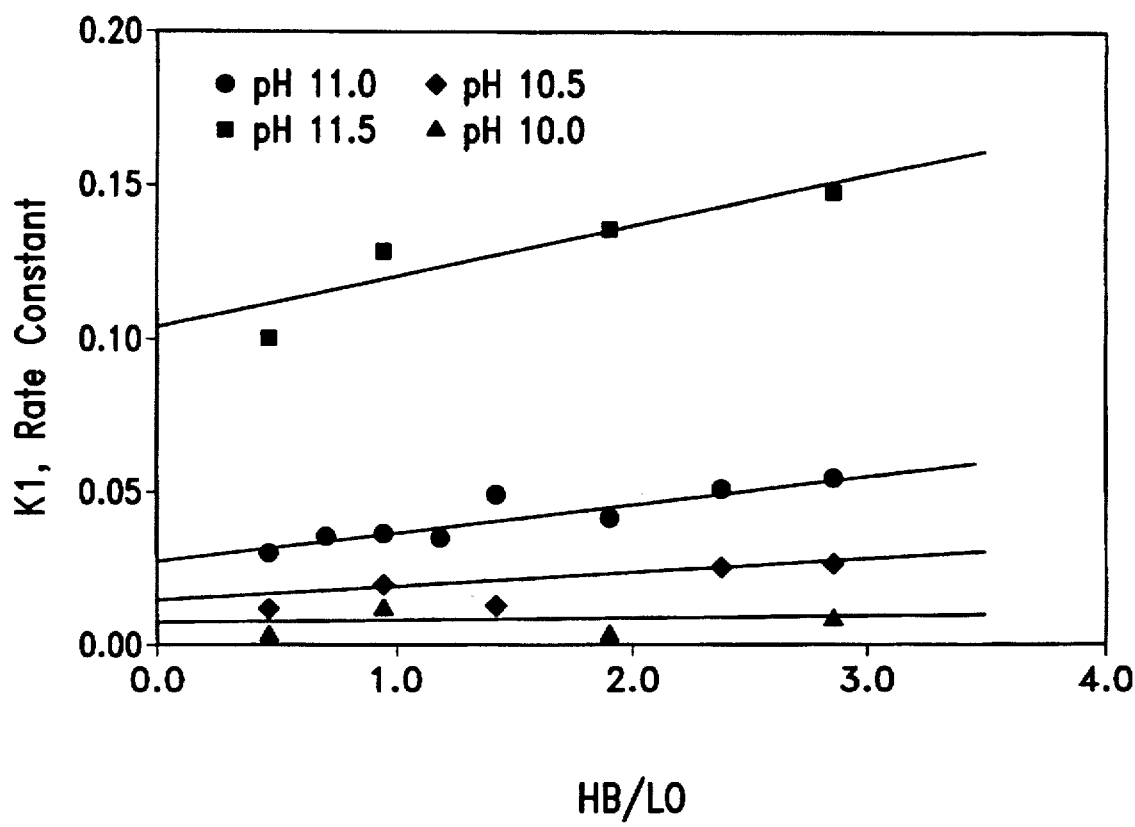
FIG. 4 shows the effect of molar ratio of boric acid to lactose on rate constant at various pH levels; 70° C. HB=boric acid concentration, $L_o$=initial lactose concentration.

Four reaction variables were investigated: temperature, pH and concentrations of lactose and the complexing agent boric acid. The effects of temperature and lactose concentration on equilibrium was studied (FIG. 2). While the reaction has been shown to occur at a temperature range of 50–85° C., there is a slight maximum in the range of 70–75° C. The effect of pH and catalyst was studied at 70° C. In a series of experiments the rate constant, $k_1$, and equilibrium values were determined as a function of molar ratio of boric acid to initial lactose concentration. The effect of complexing agent ratio on equilibrium conversion is shown in FIG. 3. The equilibrium increases rapidly with molar ratio until the ratio reaches about 1.0, then it gradually drops off. Within the range of pH about 10.5 to about 11.5, pH exerts little or no effect on the equilibrium conversion. At lower pH levels the reaction simply does not proceed and at higher pH levels there is significant caramelization and difficulty in controlling the reaction. The maximum conversion occurs at a molar ratio of about 1.0 in the pH range of about 10.5 to about 11.5. At a pH of about 11.0 and a molar ratio of boric acid to lactose of about 1.0, the conversion is about 75%. At pH 10.5 to 11.5, the rate constant $k_1$ increases slightly with molar ratio (FIG. 4). The increase is very slight relative to the effect of temperature and pH on the rate constant and is not sufficient to change the conclusion that the reaction should be run at a molar ratio of about 1.0. FIG. 4 also shows that at pH 10.0 the rate decreases slightly with the ratio and that the value of $k_1$ increases with pH.

It has thus been found that a first order kinetics model adequately describes the isomerization of lactose to lactulose in the presence of boric acid. The model uses two reactions—the first is the isomerization of lactose and complexation with boric acid and the second is the breaking of the complex and release of lactulose. The rate controlling reaction is the formation of a boric acid-lactulose complex. Optimum reaction conditions include a molar ratio of boric acid to lactose of about 1.0 and a pH of about 11. The equilibrium conversion of lactulose based on the initial concentration of lactose is about 75%.

The second phase of the project was the development of a continuous reactor system for the production of lactulose from lactose (Kozempel and Kurantz. 1994. *J. Chem Tech. Biotechnol.* vol. 59, pp. 265–269, herein incorporated by reference). The reactor section of the system is comprised of three reactors in series (FIG. 1). The first two are continuous stirred tank reactors (CSTR-A 2 and CSTR-B 3) followed by a double pass tubular reactor (TR-C 4). Flow through the reactor is controlled by metering pumps or a centrifugal pump connecting CSTR-B 3 and TR-C 4. The reaction mixture to CSTR-B 3 is recirculated to create very high agitation by using a recycle stream and a throttling valve.

From the tubular reactor 4, the reaction mixture goes to a cooler 5 to cool the product stream below room temperature. Tap water may be used as the cooling medium. From the cooler 5, the cooled mixture undergoes pH adjustment in order to split the lactulose-borate complex. Illustrated in FIG. 1 is a pH adjustment tank 6 where sufficient acid, such as HCl, is added with stirring to lower the pH to about 2 to about 3. Alternatively, an ion exchange chromatography column may also be utilized for this purpose and has the advantage of avoiding salt formation.

The reaction product from the reactors is about 20% solids containing 1.5% boric acid (dry weight basis, dwb). Lactulose is normally sold as a syrup containing about 55% solids, and permitted boric acid levels are in the range of 1–5 ppm, thus necessitating removal of virtually all the boric acid from the reaction mixture and concentration of the product. This stage of the process is carried out in the separation section of the system which is comprised of a crystallizer 7, a filter 8 and an evaporator 10 (FIG. 1).

Crystallization of some of the boric acid from the reaction product after evaporation concentrates the solids, however the solution becomes very viscous and impossible to filter satisfactorily. It was found that successful removal of boric acid could be accomplished by continuous operation of the system. By removing the boric acid solids continuously, the mixture never gets too viscous. The reaction product leaves the pH adjusting tank 6 in the form of a chilled fluid mixture comprising lactulose and boric acid at low pH and enters the crystallizer 7 where the mixture is stirred in order to allow the formation of solids. The solution must be monitored such that a maximum of about 63% solids is achieved. As the concentration approaches the maximum, the mixture is pumped through a filter 8 to remove as much of the solid component as possible, then through a surge tank 9 and into an evaporator 10 to concentrate the amount of solids in the mixture. Again, the solution must be monitored so that a maximum of about 63% solids is present in the mixture. Monitoring the solids concentrations at these two points is critical because higher concentrations causes the system to clog with crystals, thus freezing and shutting down the system completely. At that point, the concentrate is returned to the crystallizer 7 where it is added to fresh feed incoming from the pH adjusting tank 6. Thus the content of the crystallizer 7 is present as a slurry with boric acid crystals present at all times to act as nuclei to precipitate the formation of additional crystals in the incoming product stream. The amount of crystals generated by the fresh feed is sufficient to produce new crystals but insufficient to inordinately increase the viscosity of the slurry. In effect, a differential amount of boric acid is fed and removed in each pass through the separation section. By continuously cycling mixture from the evaporator 10 back into the crystallizer 7, it is possible to both increase the efficiency of the crystallization step and to control the amount of solids in the slurry, a key element of the separation process.

As shown in FIG. 1, the filtrate may also be pumped into the final separation section. The effluent from the process is about 4% boric acid (dwb) or 2.2% in a 55% syrup. In order to reduce the boric acid concentration to the required 1–5 ppm, a double column liquid chromatography system 11 is employed. The first column is a ligand exchange column where any remaining lactulose-borate complex is split and the two components separated. The separation achieved is not sufficient, however, to effectively separate the two components upon elution from the column, so the effluent is then passed through a second column, a size exclusion column, which is capable of separating the lactulose component from the borate component.

The novel method is carried out in two phases: (1) the reaction phase and (2) the recovery phase. In the reaction phase, (a) lactose and boric acid are mixed with stirring in alkaline solution for a time sufficient for isomerization of lactose to lactulose and complexation of lactulose to boric acid to occur, (b) the reaction mixture is cooled and (c) the pH of the reaction mixture is adjusted to an acidic pH.

In step (a), lactose and boric acid are mixed in a molar ration of about 1.0 in an alkaline solution. Using FIG. 1 as an exemplary system, feed tank 1 is filled to level with water, and lactose is added with agitation. Boric acid is added to the lactose solution, followed by the addition of base to adjust the pH. The preferred base is NaOH, and most of the lactose dissolves when the pH reaches about 9.5. A small amount of the lactose remains undissolved. An effective pH range is from about 9.5 to about 12.0, however a pH of about 11.0 is preferred.

The lactose-boric acid mixture flows into the reactor system comprising CSTR-A 2, CSTR-B 3 and TR-C 4. A flow rate of about 0.50 kg/ml to about 0.55 kg/ml may be effectively utilized. At this flow rate, the mixture remains in the reactors an average of about 40 min to about 45 min, sufficient time to allow isomerization and complexation to occur. An effective reaction temperature ranges from about 70° C. to about 75° C., preferably about 71° C.

At this point, the mixture contains reaction product lactulose-borate complex. The mixture flows into the cooler 5 where it is cooled to a temperature below room temperature. An effective temperature range is from about 5° C. to about 38° C. preferably about 13° C.

After the mixture is sufficiently cooled, it is fed into pH adjusting tank 6 where the pH is adjusted to an acidic pH, about 1.0 to about 4.0, preferably about 2.8.

At this point the reaction phase is complete, and the recovery phase of the process begins. A batch process may also be utilized for the isomerization and complexation reactions and successfully fed into the novel recovery system; however, the continuous process as described is more desirable from an efficiency and cost-effectiveness standpoint.

The chilled product mixture enters the crystallizer 7 and remains for a time sufficient for crystallization of boric acid to occur, at which point the mixture flows through the filter 8 for removal of the bulk of the boric acid in the form of crystals. Any effective type of filter may be utilized; however, continuous filters such as belt or drum filters are preferred for the continuous process.

When the product mixture leaves the filter, there are two options available. First, the filtrate may enter a surge tank 9 before flowing into evaporator 10 where the mixture is concentrated to a maximum of about 63% solids, in which some boric acid remains. This concentrate is recirculated into the crystallizer 7 where it is mixed with fresh feed from the pH adjusting tank. This recirculation step is critical to the effective removal of boric acid from the mixture since it provides for additional filtration of the boric acid crystals and for the presence of seed crystals which increases the efficiency of the crystallization process. In the second option, the filtrate may enter the final separation stage, i.e. the double column purification step 11. At this stage, the product mixture contains about 55% solids with about 2–3% being boric acid. The mixture passes first through a ligand exchange column where any previously uncomplexed lactulose and boric acid are split apart, then through a size exclusion column where the two components are separated. The double column system contains multiple units so that columns may be regenerated as necessary. Following the final purification, the product enters an evaporator 12 for a final concentration of product.

The following example is intended only to illustrate the invention and is not intended to limit the scope of the invention as defined by the claims.

EXAMPLE

Lactose (edible grade, Swiss Valley Farms Co., Davenport, Iowa) was added with agitation to a feed kettle filled to level with deionized water followed by the addition of boric acid (NF granular, US Borax, US Borax & Chemical Corp., Los Angeles, Calif.). NaOH (50%) was added to adjust the mixture to pH 11.0. The lactose and boric acid were present in a molar ratio of 1.0.

The mixture was then fed into the reactor system of CSTR-A and CSTR-B, each having a hold-up volume of 22.7 dm3, and TR-C, having a volume of 2.6 dm$^3$. The reaction mixture to CSTR-B was recirculated to create very high agitation by using a recycle stream and a throttling valve. The mixture remained in the reactors an average of 44 min per reactor at a reaction temperature of 71° C. The product from the reactors was 20% solids containing 15% boric acid (dwb).

The product-containing mixture was cooled to 13° C. in a cooler, followed by pH adjustment to 2.8 in a pH adjustment tank. This mixture became the feed for the separation phase carried out in a crystallizer (a 227-L scraped wall kettle, Hamilton style A, double-motion Teflon scraper agitator, Hamilton Copper and Brass Works Co., Hamilton, Ohio). Boric acid crystals formed, and the crystal-containing mixture was passed through a filter (Sparkler Filter, size 8-3, Sparkler Manufacturing Co., Conroe, Tex.) fitted with polypropylene multifilament #5-41F411 filter cloth (Tetko, Inc., Lancaster, N.Y.). The filtrate went to the evaporator at about 55% solids (a conical Kontro Ajust-o-film 0.093 m2, Petersham, Mass.) to concentrate the solution further. The concentrate was then recycled to the crystallizer.

Fresh feed from the pH adjusting tank was started to the crystallizer to maintain the volume until the system reached steady-state, which was a combination of concentrate from the evaporator and fresh feed from the pH adjusting tank.

Filtrate which contained 4% boric acid (dwb) or 2.2% in a 55% syrup was then passed onto a ligand exchange column (packed with Resin Dowex 99Ca./320, Dow Chemical Co., Midland, Mich.) to split any remaining lactulose-boric acid complex then onto a size exclusion column (packed with HW-40-C, size exclusion resin, particle size 50–100 μm Supelco, Bellefonte, Pa.). The columns were run at pH 2 with deionized water as the mobile phase.

All references cited hereinabove are herein incorporated by reference.

We claim:

1. A method for the preparation of lactulose from lactose, said method comprising
   a) mixing lactose and boric acid in a molar ratio of about 1.0 in alkaline solution to form a reaction mixture;
   b) allowing said lactose in said reaction mixture to isomerize to lactulose and complex to boric acid to form a lactulose-borate complex;
   c) cooling said reaction mixture;
   d) lowering the pH of the reaction mixture to a pH which is sufficiently acidic to split said complex;
   e) crystallizing the boric acid from the reaction mixture;
   f) filtering the reaction mixture to separate boric acid crystals from said reaction mixture to form a product mixture;
   g) evaporating said product mixture such that said product mixture is concentrated to at most about 63% solids, recirculating the concentrate to the crystallization step where said concentrate is mixed with reaction mixture from step d), or passing the product mixture through a double column chromatography unit comprised of a first ligand exchange column and a second size exclusion column; and
   h) collecting lactulose-containing eluant.

2. The method of claim 1, wherein said alkaline solution in step a) is about pH 9.5 to about pH 12.0.

3. The method of claim 2, wherein said alkaline solution is about pH 11.0.

4. The method of claim 1, wherein said reaction in step b) is carried out at a temperature of about 70° C. to about 75° C.

5. The method of claim 4, wherein said reaction is carried out at about 71° C.

6. The method of claim 1, wherein said reaction mixture is cooled in step c) to a temperature of about 5° C. to about 38° C.

7. The method of claim 6, wherein said reaction is cooled to a temperature of about 13° C.

8. The method of claim 1, wherein said pH is lowered in step d) to a pH of about 1.0 to about 4.0.

9. The method of claim 8, wherein said pH is lowered to a pH of about 2.8.

* * * * *